(12) United States Patent
Redford et al.

(10) Patent No.: US 7,315,007 B2
(45) Date of Patent: Jan. 1, 2008

(54) METHOD AND APPARATUS FOR STIFFNESS AND THICKNESS DETECTION IN MAIL SORTING SYSTEMS

(75) Inventors: Dale E. Redford, Grand Prairie, TX (US); Ottmar K. Kechel, Stockach (DE)

(73) Assignee: Siemens Dematic Corp., Grand Rapids, MI (US)

( * ) Notice: Subject to any disclaimer, the term of this patent is extended or adjusted under 35 U.S.C. 154(b) by 0 days.

(21) Appl. No.: 10/457,813

(22) Filed: Jun. 9, 2003

(65) Prior Publication Data

US 2004/0245158 A1 Dec. 9, 2004

(51) Int. Cl.
*B07C 5/00* (2006.01)
*B07C 5/34* (2006.01)

(52) U.S. Cl. .................. 209/584; 209/599; 209/900
(58) Field of Classification Search ............. 209/584, 209/900, 553, 586, 599, 699; 73/862.472
See application file for complete search history.

(56) References Cited

U.S. PATENT DOCUMENTS

| | | | | |
|---|---|---|---|---|
| 4,030,607 | A | | 6/1977 | Suda et al. .................. 209/74 |
| 4,360,108 | A | * | 11/1982 | Logothetis ................ 209/598 |
| 4,576,287 | A | * | 3/1986 | Bingham et al. .......... 209/601 |
| 4,687,106 | A | * | 8/1987 | Prins ....................... 209/552 |
| 4,886,596 | A | | 12/1989 | Sasage et al. ............. 209/539 |
| 4,953,842 | A | * | 9/1990 | Tolmie et al. ................ 271/2 |
| 5,150,894 | A | * | 9/1992 | Ricciardi ................... 271/302 |
| 5,171,403 | A | | 12/1992 | Chase et al. .............. 162/197 |
| 5,182,722 | A | * | 1/1993 | Hain ....................... 700/223 |
| 5,201,424 | A | * | 4/1993 | Hain ....................... 209/534 |
| 5,246,117 | A | * | 9/1993 | Zivley ..................... 209/586 |
| 5,297,062 | A | | 3/1994 | Cresson et al. ........... 364/564 |
| 5,637,811 | A | * | 6/1997 | Simard et al. ........... 73/865.8 |
| 5,704,246 | A | * | 1/1998 | Kruger ..................... 73/159 |
| 5,934,140 | A | | 8/1999 | Jackson et al. ............ 73/159 |
| 6,026,681 | A | | 2/2000 | Wunderer et al. .......... 73/159 |
| 6,032,517 | A | * | 3/2000 | Reisig et al. ................ 73/78 |
| 6,079,570 | A | | 6/2000 | Opplinger et al. ......... 209/630 |
| 6,135,292 | A | * | 10/2000 | Pettner .................... 209/603 |

(Continued)

*Primary Examiner*—Patrick Mackey
*Assistant Examiner*—Mark Hageman

(57) ABSTRACT

A method is provided for preventing flat mail pieces having excessive thickness or stiffness from entering a mail processing machine wherein flat mail pieces are held on opposite sides and conveyed by paired conveyor belts around one or more curves, including one curve which is the sharpest curve in the mail processing machine. Such a method includes the steps of conveying a singulated stream of flat mail pieces one at a time through a test curve upstream from the sharpest curve of the mail processing machine, the test curve including an angled section at which each mail piece tends to bend, determining the thickness of each mail piece, determining the stiffness of each mail piece by measuring deflection of one of the belts of the test curve as an end portion of the mail piece is passing through the angled section, which deflection is in excess of deflection caused by the thickness of the mail piece as it passes between the belts, and diverting a mail piece out of the mail processing machine before it reaches the sharpest curve of the mail processing machine if predetermined stiffness and thickness criteria are exceeded by the thickness and stiffness of the mail piece. The angled section defines an angle less severe than the sharpest curve, whereby a mail piece that would likely jam the mail processing machine at the sharpest curve can pass through the test curve without jamming.

7 Claims, 4 Drawing Sheets

U.S. PATENT DOCUMENTS

| | | | |
|---|---|---|---|
| 6,279,750 B1 | 8/2001 | Lohmann | 209/559 |
| 6,283,304 B1 | 9/2001 | Gottlieb et al. | 209/603 |
| 6,521,854 B2* | 2/2003 | Tanimoto | 209/586 |
| 6,655,683 B2* | 12/2003 | Engarto et al. | 271/265.04 |
| 2004/0000508 A1* | 1/2004 | Das et al. | 209/584 |
| 2004/0113358 A1 | 6/2004 | Engarto et al. | 271/262 |

* cited by examiner

METHOD AND APPARATUS FOR STIFFNESS AND THICKNESS DETECTION IN MAIL SORTING SYSTEMS

FIELD OF THE INVENTION

The present invention relates to a process for the sorting of mail and, more particularly, to a method and apparatus for determining a parameter reflecting a combination of the thickness and stiffness of mail pieces.

BACKGROUND OF THE INVENTION

The United States Postal Service, along with other private and public postal services, rely heavily on automated scanning, sorting and handling systems to process millions of mail pieces each day. These automated systems necessarily utilize specialized equipment designed to transport, scan, process and sort envelopes and other flat pieces of mail. In many cases, opposed belt and roller type conveyors are used to transport mail pieces along paths including curves, turns and transitions, in some cases conveying the mail pieces through arcuate paths with bends ranging from a few degrees up to 180°. Mail pieces comprising flat, flexible envelopes, postcards, thin brochures and similar items are normally conveyed without difficulty through such paths.

Stiffer and/or thicker mail pieces may, however, present problems when processed with such automated mail handling equipment. Mail pieces that are too stiff and/or too thick may be damaged or destroyed during the sorting process. Such mail pieces may also jam or damage the processing equipment. Likewise, mail pieces that are excessively long and stiff or long and thick can cause similar problems. Consequently, it is desirable to separate mail pieces having physical properties and dimensions that are not compatible with automated sorting and handling equipment at an early stage in the automated sorting process to avoid these problems.

Reisig U.S. Pat. No. 6,032,517 describes an arrangement for measuring the rigidity of flat items with the aid of a conveying path in which the items are transported separately by means of conveying belts, wherein the conveying path has a straight section and a curved section and wherein the conveying belts are made of an elastic material in the region of the curved section. At least one rigidity sensor is provided for measuring the deflection of the conveying belts caused by the item passing through a predetermined position of the curved section, and at least one thickness sensor is provided in the region of the straight section. An evaluation device is provided for determining the rigidity of an item passing through from the values obtained by the thickness and rigidity sensors.

In order to efficiently separate mail pieces having dimensions and physical properties incompatible with automated sorting equipment, it is desirable to consider both the thickness and the stiffness of mail pieces in determining whether a particular mail piece can be processed using a particular application to avoid unnecessary diversion of mail pieces that are suitable for automated processing. For example, a relatively thick, but flexible mail piece may be readily processed through a particular automated sorting line whereas a thin, very rigid mail piece may cause a jam, damage the machinery, or be damaged. In this instance, the thick flexible mail piece would ideally be processed, while the thin rigid mail piece would be diverted. Further, a system capable of sorting a six inch long mail piece with a given thickness and stiffness may jam with a ten inch mail piece having the same thickness and stiffness. Thus, it is desirable to consider length as a parameter when determining whether a particular mail piece can be processed using automated sorting equipment. The present invention addresses these needs.

SUMMARY OF THE INVENTION

In accordance with the invention, a method is provided for preventing flat mail pieces having excessive thickness or stiffness from entering a mail processing machine wherein flat mail pieces are held on opposite sides and conveyed by paired conveyor belts around one or more curves, including one curve which is the sharpest curve in the mail processing machine. Such a method includes the steps of:

(a) conveying a singulated stream of flat mail pieces such as letters or flats one at a time though a test curve upstream from the sharpest curve of the mail processing machine, the test curve including an angled section at which each mail piece tends to bend;

(b) determining the thickness of each mail piece;

(c) determining the stiffness of each mail piece by measuring deflection of one of the belts of the test curve as the mail piece is passing through the angled section, which deflection is in excess of deflection caused by the thickness of the mail piece as it passes between the belts; and (d) diverting a mail piece out of the mail processing machine before it reaches the sharpest curve of the mail processing machine if predetermined stiffness and thickness criteria are exceeded by the thickness or stiffness of the mail piece. The angled section defines an angle less severe than the sharpest curve of the mail processing machine, so that a mail piece that would jam the mail processing machine at the sharpest curve can pass through the test curve without jamming. In a preferred form of this method, step (b) further comprises measuring deflection of the belt from a starting position in which no mail piece is between the belts to a thickness measuring position wherein the mail piece is between the belts, but has not entered the angled section of the test curve. Step (c) then further comprises measuring additional deflection of the one belt from the thickness measuring position to a position with the mail piece positioned in the angled section of the test curve.

The invention further provides a detection apparatus for use in a mail processing system such as an OCR or bar code-based postal sorting machine. In such a machine, a singulated stream of mail pieces is conveyed through a path having one or more processing sections suitable for processing mail pieces having a thickness, stiffness or combination of thickness and stiffness falling below one or more predetermined maximum values. Mail pieces having a thickness, stiffness or combination of thickness and stiffness exceeding the one or more predetermined maximum values will tend to jam the mail processing system during conveyance around one or more curves.

The detection apparatus usable with such a system includes a pair of opposed belt conveyors adapted to convey mail pieces therebetween. The opposed belt conveyors define a test curve having first and second paths, the second path being angled from the first path. The angle is less severe than the most severe angle that will be encountered downstream in the mail processing system, such that the test curve is capable of receiving and conveying articles having a stiffness, thickness or combination of thickness and stiffness exceeding the predetermined maximum values. The detection apparatus further includes a sensor that measures the thickness and stiffness of a mail piece conveyed from the first path to the second path, and a controller connected to the sensor, the controller being programed to receive and compare the thickness and stiffness values to the predetermined values. A diverter is operatively connected to the controller such that the controller signals the diverter to separate mail pieces exceeding one or more of the predetermined values from the stream of mail pieces.

In a preferred form of this apparatus, the sensor preferably comprises a pivoting arm having a distal end in contact with an outer surface of a first belt of the belt conveyor, and a meter for measuring displacement of the pivoting arm in tandem with the first belt and transmitting a signal indicating such displacement to the controller. Suitable means may be provided for adjusting tension of the first belt so that the belt displaces when a relatively stiff mail piece is encountered. The sensor is preferably located upstream from the second path at a position where a mail piece partially disposed in the second path causes deflection of the first belt in proportion to the stiffness of the mail piece, and a mail piece disposed in the first path prior to entering the second path causes deflection of the first belt equal to the thickness of the mail piece.

A detection apparatus of the invention is most suited for direct incorporation into a larger mail processing machine, but could also be employed as a stand alone system through which mail pieces are fed prior to entry into the sorter or other mail processing system. The test angle may be half or less of the angle of the sharpest curve upstream, e.g. 10° for an upstream curve at 20°. The sensor preferably comprises a deflection sensor of some type, but an optical sensor could also be employed.

One method of the invention comprises measuring the thickness of the mail piece as the mail piece travels through the first path and then measuring the stiffness of the mail piece as the mail piece travels from the first path to the second path. The stiffness of the mail piece is measured by recording the deflection of the trailing end of the mail piece as the mail piece is conveyed from the first to the second path. The first measurement, taken when the mail piece travels through the first path, and the second measurement, taken when the mail piece travels from the first path to the second path, are transmitted to the controller. In one aspect, the controller combines the first and second measurements to obtain a combined thickness and stiffness measurement which the controller compares to one or more predetermined values. The predetermined value(s) represent combined values for a theoretical mail piece having a maximum combined thickness and stiffness suitable for transport through the curved section. The predetermined values and program logic for the comparison are preprogramed into the controller's memory. These and other aspects of the invention are discussed further in the detailed description that follows.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION

Figure 1:
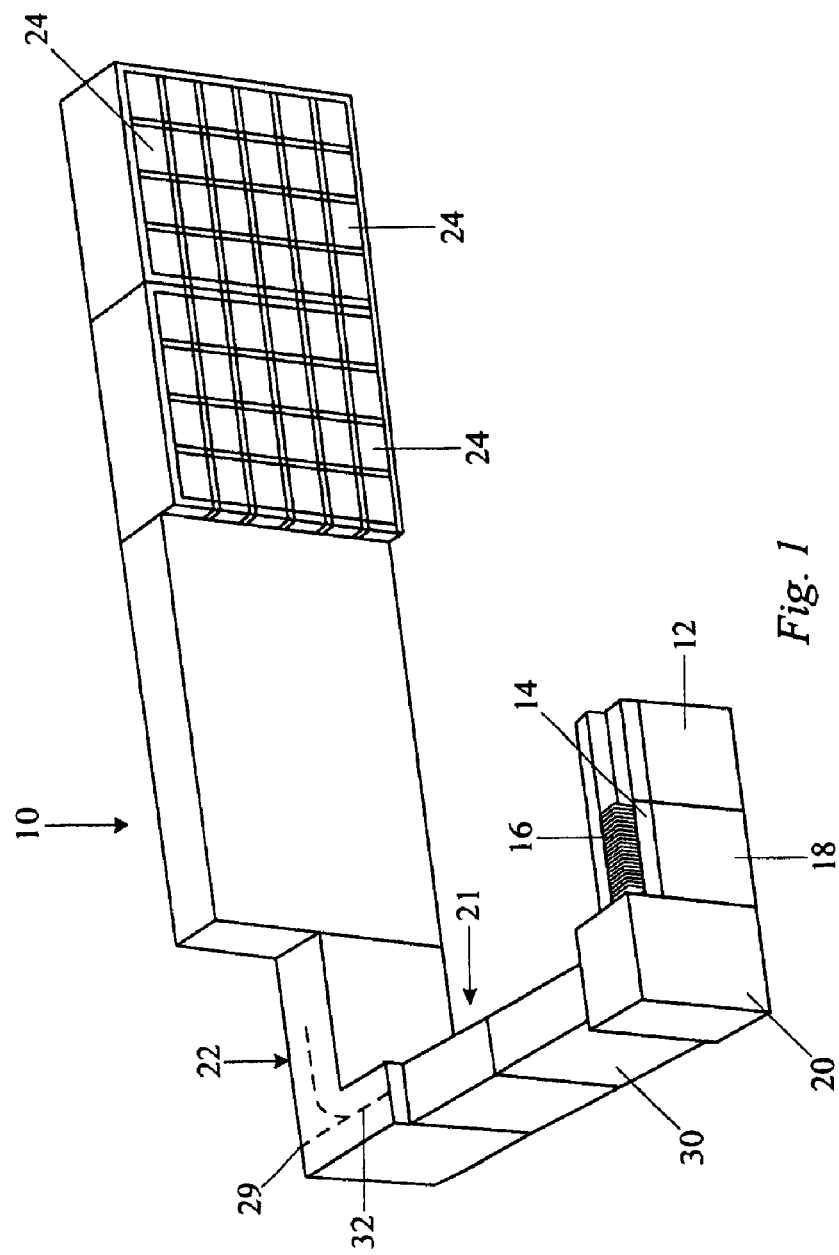
FIG. 1 is schematic representation of an automated mail sorting system employing the apparatus and method of the invention.

Referring to FIG. 1, in one variation of the invention, a mail sorting system 10 such as a DBCS machine includes a mail feeder 12 upon which a stack 14 of unsorted mail pieces 16 are loaded for processing. Mail feeder 12 includes a jogger-conveyor 18 that advances the stack 14 to a pick off apparatus 20 that feeds a singulated stream of individual mail pieces through a transport section 21 to an automated sorting section 22 which sorts the mail in one or more passes to a plurality of bins 24. In transport section 21, each mail piece is scanned for address information. As is typical, sorting section 22 is limited in terms of the thickness, stiffness and combined thickness and stiffness of mail pieces that it can process.

A detection module 30 according to the invention may be incorporated into transport section 21 between pick off 20 and sorting section 22, so that the singulated stream of mail pieces 16 pass through module 30 before being conveyed to sorting section 22 for processing. A divert 32 for diverting rejected mail pieces is positioned between module 30 and sorting section 22. A controller activates divert 32 upon receiving a signal from detection module 30 indicating that a mail piece is too stiff, too thick, too long or short, or has a combination of stiffness, thickness and length that renders the mail piece unsuitable for processing by sorting section 22. In the illustrated embodiment, divert 32 is conveniently located at one end of transport section 21 just upstream from an entry end of sorting section 22 and diverts mail pieces rejected as a result of testing by causing them to continue traveling in a straight line and be ejected from one end 29 of sorter 10, rather than be conveyed around a 90° curve as shown for non-diverted mail entering sorting section 22. This arrangement avoids potential jamming of the reject that might occur if an angled divert were employed.

Figure 2:
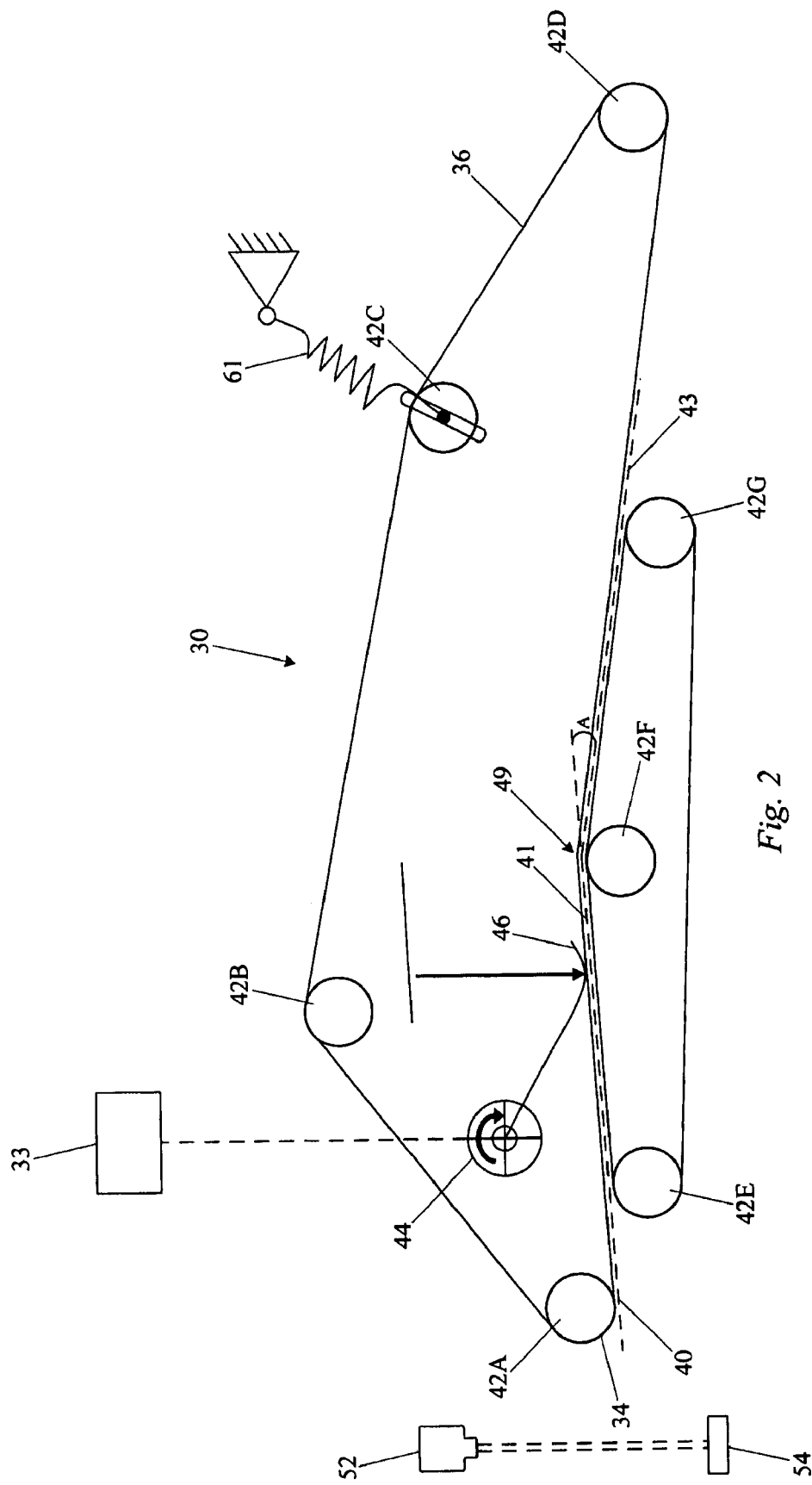
FIG. 2 is a side view of a thickness and stiffness detector according to the invention.

Turning to FIG. 2, a detection module 30 of the invention includes an opposed belt conveyor 34 with first and second conveyor belts 36 and 38 respectively, which form an angled horizontal or vertical conveying path schematically represented as dashed line 40. The angled conveying path or test section includes first and second path segments 41, 43 through which mail pieces 16 are conveyed before sorting. As illustrated, belt 36 passes over a plurality of asymmetrically arranged rollers 42a-d that define a polygon with one long side or leg between rollers 42a and 42d. Roller 42c is mounted with a spring loaded tensioning device 61 for maintaining the tension on belt 36. The tension on the belt system should be set at a value which permits deflection when a mail piece has sufficient stiffness. The specific tension value can be determined by trial and error, with mail pieces known to cause jamming problems for the mail processing system on which test curve 30 will be mounted, as further described below. At least one of rollers 42a-d is a conventionally powered drive roller for driving the belt. Similarly, conveyor belt 38 extends around a plurality of rollers 42e-g, at least one of which is a powered drive roller. Conveyor belts 36, 38 are preferably driven at a constant speed to facilitate measurement of the length of the mail pieces carried by the conveyor by means of a photo detector as described below.

Conveying path segments 41 and 43 define an angle A, which is specifically configured to be less severe than any angle or bend through which the mail pieces are conveyor or transported in sorting section 22. Typically, A is in the range of from about 5 to 30 degrees. Angle A should be sufficiently small so that mail pieces having a thickness, stiffness or combination of thickness or stiffness exceeding the maximum values for mail pieces suitable for processing in sorting system 22 can be conveyed through the test curve without difficulty. It is preferred that A be half or less than the sharpest curve, i.e. the maximum angle or bend through which mail pieces are carried downstream in the sorting machine.

A sensor 44, such as an electronic shaft encoder or similar device, includes an arm 46 positioned adjacent to or within the perimeter of belt conveyor 36 such that upward displacement of the lower flight of belt 36 can be measured as mail pieces are transported along path 40. As shown in FIG. 2, arm 46 is in the "zero" or no displacement position. Although as illustrated, sensor 44 is a shaft encoder, the sensor may be any device that converts displacement of arm 46 to a signal that can be subsequently transmitted to controller 33. Controller 33 may be a programable linear controller, microprocessor or process control computer.

Module 30 also includes one or more light sources 52 and photo receptors 54 positioned such that the beam of light emitted by source 52 is interrupted by a mail piece entering module 30. Photo receptor 54 is connected and configured to transmit a signal to controller 33 when the beam from light source 52 is broken, thereby signaling controller 33 when a mail piece enters module 30 and enabling controller 33 to determine the length of the mail piece based on the period of amount of time that the mail piece blocks the beam.

Figure 5:
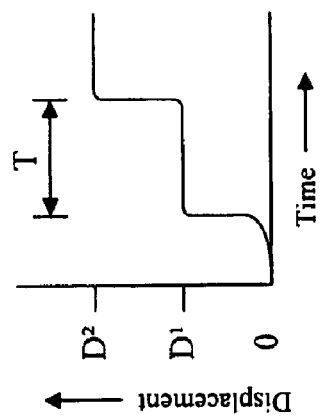
FIG. 5 is a graphical representation of thickness and stiffness measurements taken in accordance with a method of the invention.
Figure 3:
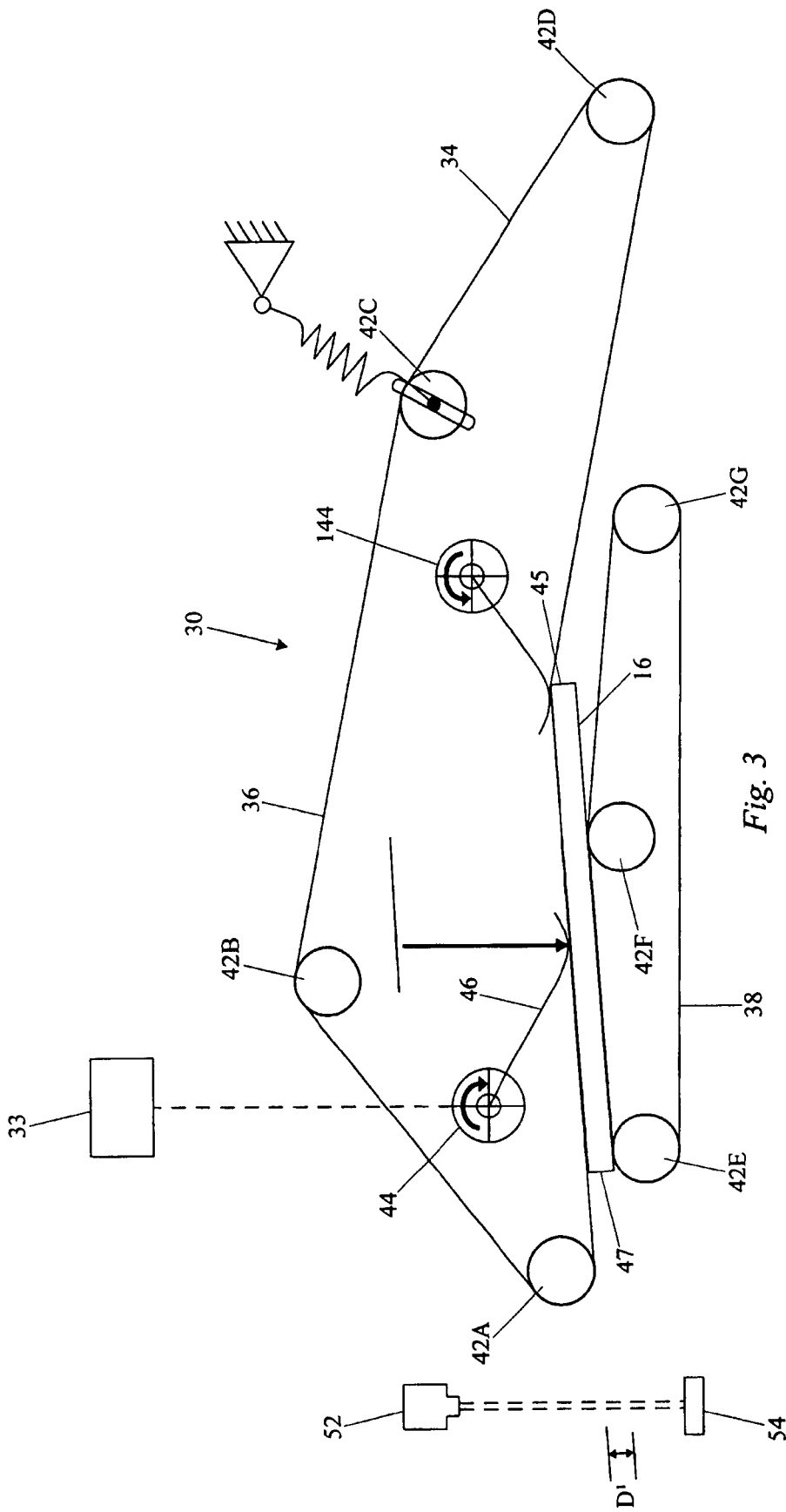
FIG. 3 is a side view of the detection apparatus of FIG. 2 wherein a mail piece is illustrated in a first position in the apparatus.
Figure 4:
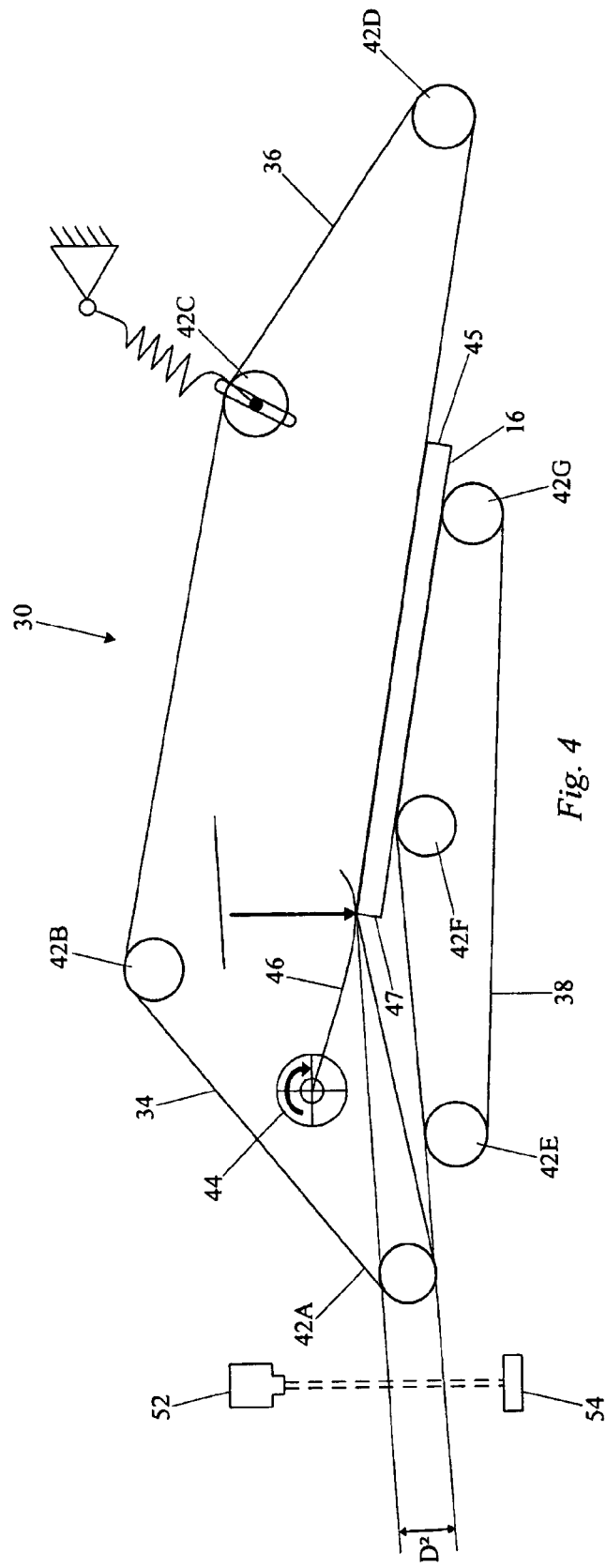
FIG. 4 is a side view of the detection apparatus of FIGS. 2 and 3 wherein a mail piece is illustrated in a second position in the apparatus.

Referring to FIGS. 3 through 5, in operation a mail piece 16 is conveyed between conveyor belts 36 and 38 along path segment 41, initially displacing belt 36 a distance $D_1$ equal to the thickness T of the mail piece. Arm 46 is simultaneously deflected a distance $D_1$ and sensor 44 transmits a signal to controller 33 proportional to the deflection. After the initial deflection, arm 46 remains relatively stationary until mail piece 16 is forced to change direction as the mail piece is conveyed further, entering an angled section 49 while traveling from segment 41 to segment 43. As shown in FIG. 4, depending on the stiffness and the length of the mail piece, the force applied to the leading end 45 of the mail piece as the mail piece changes direction causes the trailing end 47 of the mail piece to deflect or displace belt 36 a distance $D_2$. Arm 46 is displaced a corresponding distance and sensor 44 sends a corresponding signal to controller 33.

$D_2$ represents the displacement of belt 36 resulting from a combination of the thickness and the stiffness of mail piece 16. In accordance with the invention, the difference between the displacement $D_2$ representing the combined effect of the thickness and stiffness of mail piece 16, and $D_1$, which reflects the thickness of mail piece 16, is used as a measure of the relative stiffness of mail piece 16. As illustrated in FIG. 5, the change from zero displacement to an initial thickness displacement $D_1$ and then to the subsequent maximum stiffness displacement $D_2$ can be derived from the changes that occur as mail piece 16 passes through the test curve.

The test curve is designed on the basis of the relationship $TH=D_2 \circ C$, wherein TH is a combined stiffness/thickness value threshold of the most severe curve in the sorting system, and C is multiplication factor which scales up the measured value of $D_2$. Any mail piece exceeding the threshold value of TH is to be rejected. The value of C can be determined based on empirical results as described further below.

After $D_1$ and $D_2$ have been determined and transmitted to controller 33, in one variation, controller 33 utilizes a lookup table to determine whether the mail piece is suitable for processing in sorting section 22:

| Thickness | Stiffness | Combined Stiffness/thickness | Result |
|---|---|---|---|
| >14 mm | — | >=14 | Reject |
| <12 mm | <2 mm | <14 | Pass |
| <10 mm | <4 mm | <14 | Pass |
| <8 mm | <6 mm | <14 | Pass |
| <6 mm | <8 mm | <14 | Pass |
| <4 mm | <10 mm | <14 | Pass |
| <2 mm | <12 mm | <14 | Pass |
| — | >14 mm | >=14 | Reject |

Using the above table, controller 33 will signal divert 32 to divert any mail piece having a thickness greater than 14 mm, regardless of the stiffness of the mail piece. Likewise, any mail piece having an equivalent stiffness greater than 14 mm is diverted irrespective of the thickness of the mail piece. Mail pieces having a combined thickness and stiffness less than 14 mm are deemed acceptable for automated processing, and will be conveyed to automated sorting section 22. One or more preprogramed equations or algorithms may be substituted for the decision table described above, in which case such algorithms or equations would be the functional equivalent of a decision table.

Different mail handling equipment and systems will have different limits on the thickness and stiffness of mail pieces that may be processed. In order to adapt detection module 30 to different systems, the maximum values for thickness, stiffness and combinations thereof are determined for the particular application. For example, if the combined thickness and stiffness for a particular automated sorting system is determined to be 28 mm, a factor C=2 could be used with the decision table above.

In some instances, the determination of whether a mail piece is suitable for processing through a particular machine or machines may depend more heavily on thickness than on stiffness or vice versa. In these applications, it may be necessary to use separately derived constants to normalize values for thickness and stiffness and/or compare observed values of thickness and stiffness, whereas in other applications it may be sufficient to utilize a combined value to determine if a mail piece is suitable for processing.

In another variation of the invention, the length of each mail piece is used as a parameter to determine the suitability of the mail piece for processing through an automated mail handling system. The length of the mail piece is determined by multiplying the period of time that the beam from source 52 is obstructed by the linear velocity of belts 36, 38 as the mail piece passes photo receptor 54. The length of the mail piece can be used independently or in combination with the thickness and stiffness measurements to determine whether a particular mail piece is suitable for automated processing. For example, a mail piece having a stiffness of 6 mm and a length of 150 mm may be suitable for processing, whereas a mail piece having a stiffness of 10 mm and a length of 150 mm may present a risk of jamming the processing equipment. Where thickness, stiffness and length are each used to determine the suitability of a mail piece for processing, the rejection decision table will include maximum acceptable values for thickness, stiffness and length, or a more advanced mathematical model could be used, such as a three-dimensional function (x, y, z=thickness, stiffness, length) wherein each point corresponds to a particular combination of stiffness, thickness and length.

In a preferred system that takes length as well and mail piece thickness and stiffness into account, the conditions for rejection may be based on the measured length of stiff mail piece segments rather than the length of the entire mail piece as in the example above. Controller 33 is programmed to record the data to plot the entire curve of displacement versus time as shown in FIG. 5. Controller 30 determines for each passing mail piece both the maximum deflection (combined thickness+stiffness) as well as the length of time the mail piece was at (or near) maximum deflection. This length of time represents the length of the stiff segment in the mail piece, as would be observed when a rigid object is enclosed in an envelope and mailed. The time and maximum or average deflection observed during that time are recorded and compared to a table or formula giving the conditions for rejection. Such conditions may permit a short highly stiff segment to pass, but reject a mailpiece with a longer, less stiff segment.

The arrangement shown in FIGS. 2-4 assumes essentially uniform stiffness along the entire length of a mail piece, and is effective mainly to measure the stiffness of the rear half of each mail piece. In order to generate a more complete time versus displacement curve, measures should be taken to measure the stiffness of the front end of each mail piece. For this purpose, a second sensor 144 (FIG. 3) can be positioned on the other side of roller 42$f$ which defines the angle A, the point at which the mail piece changes direction in the test curve. The curve is then generated based on the results from both of sensors 44, 144, using sensor 44 for the rear half of the mail piece and sensor 144 for the front half.

Jamming of a mail sorting machine is a complex phenomenon, and it may be most preferable to program controller 5 on the basis of empirical test results. Accordingly, a series of items known to commonly cause the sorter to jam are fed through module 30 and used as the basis for defining the rejection conditions. During sorting, any mail piece meeting the rejection condition will be rejected and diverted out of the system. This method of programming controller 33 permits more specific definitions of reject conditions that conform to actual experience, and may take length of stiff segments into account, thereby leading to better results than criteria based on general estimates. According to a further version of such a method, the entire curve of displacement versus time for a reject item is recorded as a reference curve, and the curve generated by each passing mail piece during the sorting run is compared to each reference curve by suitable means such as a digital signal processor. If the correspondence measured is high, the item is presumed to be of the same kind as the item used to generate the reference curve, and the item is rejected.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is, therefore, intended that the appended claims encompass any such modifications or embodiments.

The invention claimed is:

1. A method of preventing flat mail pieces having excessive thickness or stiffness from entering a mail processing machine wherein flat mail pieces are held on opposite sides and conveyed by paired conveyor belts around one or more curves, including one curve which is the sharpest curve in the mail processing machine, comprising the steps of:
   (a) conveying a singulated stream of flat mail pieces one at a time though a test curve upstream from the sharpest curve of the mail processing machine, the test curve including an angled section at which each mail piece tends to bend;
   (b) determining the thickness of each mail piece;
   (c) determining the stiffness of each mail piece by measuring deflection of one of the belts of the test curve as the mail piece is passing through the angled section, which deflection is in excess of deflection caused by the thickness of the mail piece as it passes between the belts; and
   (d) diverting a mail piece out of the mail processing machine before it reaches the sharpest curve of the mail processing machine if predetermined criteria are exceeded, the predetermined criteria including a maximum thickness, a maximum stiffness, and one or more combined stiffness and thickness values wherein the thickness is less than the maximum thickness and the stiffness is less than the maximum stiffness, wherein the angled section defines an angle less severe than the sharpest curve, whereby a mail piece that would jam the mail processing machine at the sharpest curve can pass through the test curve without jamming, and the predetermined stiffness and thickness criteria are based on a relationship between the test curve and the sharpest curve, which relationship is TH=$D_2$*C, wherein TH is a combined stiffness/thickness value threshold of the sharpest curve, $D_2$ is the combined thickness and stiffness of a mail piece, and C is a multiplication factor which scales up the value of $D_2$.

2. The method of claim 1, wherein step (b) further comprises measuring deflection of the one belt from a position in which no mail piece is present in the test curve to a thickness measuring position wherein the mail piece is present at the one belt but is not in the angled section of the test curve.

3. The method of claim 2, wherein step (c) further comprises measuring additional deflection of the one belt from the thickness measuring position to a position with the mail piece in the angled section of the test curve.

4. The method of claim 1, further comprising:
   measuring the length of each mail piece as it passes through the test curve; and
   diverting the mail piece out of the mail processing machine before it reaches the sharpest curve of the mail processing machine if predetermined length criteria are exceeded by the mail piece.

5. The method of claim 1, further comprising measuring the length of each mail piece as it passes through the test curve and diverting a mail piece out of the mail processing machine before it reaches the sharpest curve of the mail processing machine if predetermined stiffness and length criteria are exceeded by the length and stiffness of the mail piece.

6. The method of claim 1, wherein the mail processing machine is a mail sorter.

7. The method of claim 6, wherein the mail sorter includes a feeder having a pickoff mechanism that removes mail pieces one by one from a stack, a sorting section including multiple diverts which comprise the curves of the mail processing machine, and a straight transport section in which mail pieces are transported from the feeder to the sorting section, wherein the diverting step comprises diverting a mail piece from a curved path leading to the sorting section to a straight path leading out of the mail sorter.

* * * * *